United States Patent [19]

Byrd et al.

[11] Patent Number: 5,569,228
[45] Date of Patent: Oct. 29, 1996

[54] C-FOLD RELEASABLE WRAPPER

[75] Inventors: Alan E. Byrd, Hamilton; Thomas W. Osborn, III, Cincinnati; Gary E. McKibben, Middletown, all of Ohio

[73] Assignee: The Procter & Gamble Company, Cincinnati, Ohio

[21] Appl. No.: 459,372

[22] Filed: Jun. 2, 1995

Related U.S. Application Data

[63] Continuation of Ser. No. 348,282, Nov. 30, 1994, abandoned, which is a continuation of Ser. No. 247,912, May 23, 1994, abandoned, which is a continuation of Ser. No. 990,825, Dec. 14, 1992, abandoned, which is a continuation of Ser. No. 533,614, Jun. 5, 1990, abandoned.

[51] Int. Cl.$^6$ ............... A61F 13/15; A61B 17/06
[52] U.S. Cl. ............ 604/385.1; 604/387; 604/389; 206/438
[58] Field of Search ............ 604/385.1, 385.2, 604/386, 387, 389, 390, 391; 206/438, 440

[56] References Cited

U.S. PATENT DOCUMENTS

| | | | |
|---|---|---|---|
| 3,674,195 | 7/1972 | Stone | 206/440 |
| 3,688,771 | 9/1972 | Werner | 604/386 |
| 3,967,729 | 7/1976 | Tanner, II | 206/440 |
| 3,970,087 | 7/1976 | Castaneda | 204/387 |
| 3,973,567 | 8/1976 | Srinivasan et al. | 128/290 R |
| 4,182,336 | 1/1980 | Black | 604/386 |
| 4,285,343 | 8/1981 | McNair . | |
| 4,312,085 | 1/1982 | Potter . | |
| 4,402,689 | 9/1983 | Baum | 604/387 |
| 4,555,022 | 11/1985 | Eagon et al. | 206/438 |
| 4,556,146 | 12/1985 | Swanson et al. | 206/440 |
| 4,581,027 | 4/1986 | Alvarado | 604/385 |
| 4,608,047 | 8/1986 | Mattingly | 604/387 |
| 4,735,316 | 4/1988 | Froidh et al. | 206/438 |
| 4,738,678 | 4/1988 | Paulis . | |
| 4,765,477 | 8/1988 | Froidh et al. | 206/438 |
| 4,781,712 | 11/1988 | Barabino et al. | 604/385.1 |
| 4,846,828 | 7/1989 | Mendelsohn | 604/387 |
| 4,857,066 | 8/1989 | Allison | 604/385.1 |
| 4,917,675 | 4/1990 | Taylor et al. . | |
| 5,088,993 | 2/1992 | Gaur | 604/386 |

FOREIGN PATENT DOCUMENTS

| | | |
|---|---|---|
| 0314535A1 | 9/1988 | European Pat. Off. . |
| 0299532 | 1/1989 | European Pat. Off. ........ 604/385.1 |
| 0313426A1 | 4/1989 | European Pat. Off. . |
| 0350924A3 | 1/1990 | European Pat. Off. . |
| 0357000A1 | 3/1990 | European Pat. Off. . |
| 2081100 | 2/1982 | United Kingdom . |
| WO89/02729 | 9/1987 | WIPO . |
| WO88/04546 | 6/1988 | WIPO . |
| WO88/10219 | 12/1988 | WIPO . |
| WO89/02728 | 4/1989 | WIPO . |
| WO90/01311 | 2/1990 | WIPO . |

OTHER PUBLICATIONS

European Patent Office PCT Search Report filed in counterpart EPO application file No. US/91 03580, dated May 23, 1991.

*Primary Examiner*—John G. Weiss
*Assistant Examiner*—K. M. Reichle
*Attorney, Agent, or Firm*—Edward J. Milbrada; Jeffrey V. Bamber; Steven W. Miller

[57] ABSTRACT

Disclosed is a sanitary napkin and releasable wrapper package. The releasable wrapper is folded about the longitudinal side margins of the sanitary napkin in a C-fold so that both faces of the sanitary napkin are protected and a relatively smaller package is produced than if the releasable wrapper extends laterally beyond the longitudinal side margins of the sanitary napkin. The releasable wrapper and sanitary napkin may be trifolded about spaced-apart, laterally oriented fold lines to produce a discrete single use package. Several variations, including flapped and asymmetric embodiments, are illustrated.

1 Claim, 3 Drawing Sheets

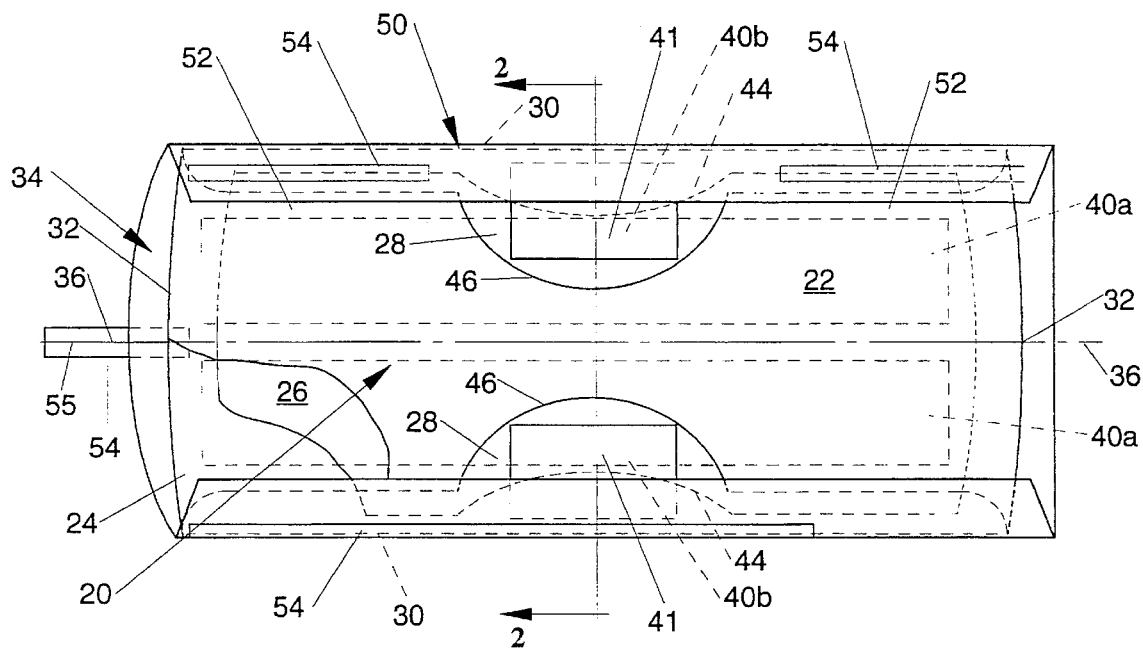
Fig. 1
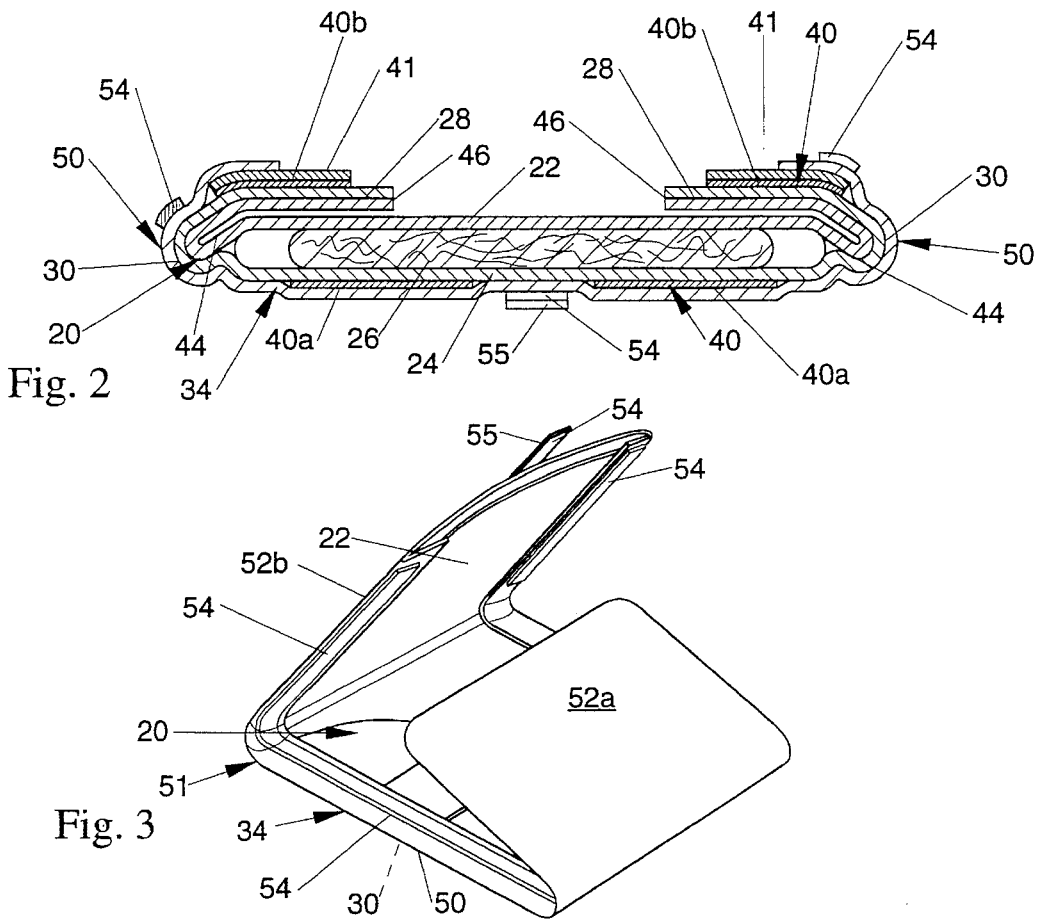
Fig. 2
Fig. 3

C-FOLD RELEASABLE WRAPPER

This is a continuation of application Ser. No. 08/348,282, filed on Nov. 30, 1994, which is a continuation of application Ser. No. 08/247,912, filed on May 23, 1994, which is a continuation of application of Ser. No.07/990,825, filed on Dec. 14, 1992, which is a continuation of application Ser. No. 07/533,614 filed on Jun. 5, 1990,all now abandoned.

FIELD OF THE INVENTION

This invention is directed to sanitary napkins and more particularly to individually packaged sanitary napkins.

BACKGROUND OF THE INVENTION

Sanitary napkins used to collect vaginal discharges are well known in the art. As disclosed in U.S. Pat. No. 4,556,146 issued Dec. 3, 1985, to Swanson et al., such sanitary napkins are frequently individually packaged for the convenience of the user as she travels, etc. In the Swanson et al. patent, disclosed is a trifolded wrapper which packages a sanitary napkin, covers adhesive on the outwardly oriented face of the backsheet, and may be used for disposing of a used article.

However, one drawback suffered by the Swanson et al. teaching is that the package is larger than necessary, due to the lateral extension of the wrapper beyond the longitudinal side margins of the sanitary napkin. Such extension is necessary for sealing purposes. This arrangement results in a package which is less compact than desirable, requires more space in a purse etc., and, thus, provides less discretion for the user.

Other trifolded arrangements are known, such as that disclosed in U.S. Pat. No. 3,604,423 issued Sep. 14, 1971 to Fraser and in International Publication WO 89/02728 published Apr. 6, 1989 in the name of Froidh et al. However, these teachings suffer from the drawback that conveniently removable packaging used in conjunction with a small individually packaged sanitary napkin is not taught.

Discarding used sanitary napkins enveloped in the packaging is further taught in the art. For example, International Publication WO 89/02729 published Apr. 6, 1989 in the name of Pigneul and U.S. Pat. No. 4,608,047 issued Aug. 26, 1986 to Mattingly disclose two packaging arrangements suitable for this purpose.

Accordingly, it is an object of this invention to provide an individually packaged sanitary napkin. It is further an object of this invention to provide an individually packaged sanitary napkin which is easy for the user to manipulate from the packaged arrangement to the wearing arrangement. It is also an object of this invention to provide a relatively smaller package which provides enhanced discretion for the user. It is also an object of this invention to provide an individually packaged sanitary napkin with packaging that also protects exposed adhesive prior to the first use by the wearer. Finally, it is an object of this invention to provide an individually packaged sanitary napkin having packaging which may be used for disposal of a used product.

BRIEF SUMMARY OF THE INVENTION

The present invention comprises a sanitary napkin having two mutually opposed major faces, two longitudinal and two lateral side margins. The sanitary napkin has a liquid pervious topsheet, a liquid impervious backsheet joined to the topsheet, an adhesive patch joined to the outwardly oriented face of the backsheet and an absorbent core between the topsheet and the backsheet. A releasable wrapper having one end juxtaposed with a lateral side margin of the sanitary napkin and releasably affixed to at least one major face of the sanitary napkin wraps at least one longitudinal side margin in a C-fold.

In one embodiment, the sanitary napkin has two flaps, each with a proximal end joined to one longitudinal side margin of the sanitary napkin. Each flap has two mutually opposed faces. One face is generally coextensive of the topsheet. The other face is generally coextensive of the backsheet and has an adhesive patch used for attachment to the undergarment. The flaps are folded over either the topsheet or the backsheet. The releasable wrapper is releasably affixed to the adhesive of the backsheet and has two longitudinal side margins. The releasable wrapper is wrapped around said longitudinal side margins of the sanitary napkin in a C-fold so that the longitudinal side margins of the releasable wrapper are intermediate the proximal ends of the flaps.

BRIEF DESCRIPTION OF THE DRAWINGS

While the Specification concludes with claims particularly pointing out and distinctly claiming the present invention, it is believed the invention will be better understood from the following description taken in conjunction with the accompanying drawings wherein like parts are given the same reference numeral, analogous parts are designated with a prime symbol and:

FIG. 1 is a top plan view of a flapped sanitary napkin and releasable wrapper with portions cut anyway, according to the present invention, and showing a different adhesive configuration at each longitudinal edge of the releasable wrapper;

FIG. 2 is a vertical sectional view taken along lines 2—2 of FIG. 1;

FIG. 3 is a perspective view of a wrapper and a sanitary napkin not having flaps, in a partially trifolded configuration;

DETAILED DESCRIPTION OF THE INVENTION

Figure 4:
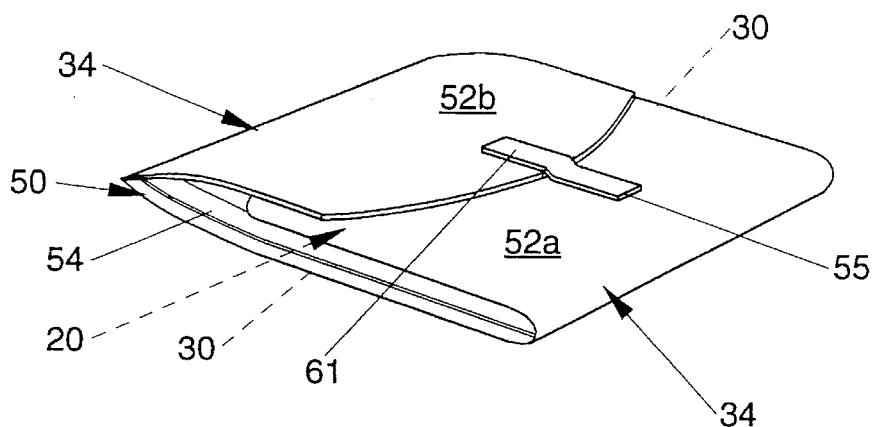
FIG. 4 is the sanitary napkin and wrapper according to FIG. 2 shown in a fully trifolded configuration.

As shown in FIG. 1, the invention comprises a disposable absorbent article, particularly a sanitary napkin 20. The sanitary napkin 20 is used to collect vaginal discharges, such as menses, and to prevent soiling of the wearer's clothing by such discharges. The sanitary napkin 20 features a liquid pervious topsheet 22, a liquid impervious backsheet 24, and an absorbent core 26 intermediate the topsheet 22 and the backsheet 24. The perimeter of the central portion of sanitary napkin 20 is defined by the two longitudinal side margins 30 and two lateral side margins 32. If desired, the sanitary napkin 20 may further comprise at least one flap 28 extending laterally beyond a longitudinal side margin 30 of the sanitary napkin 20, and preferably two symmetrically opposite flaps 28, one extending laterally beyond each longitudinal side margin 30 of the sanitary napkin 20. The sanitary napkin 20 is superimposed on a releasable wrapper 34. The releasable wrapper 34 underlays and is releasably affixed to the outwardly oriented face of the backsheet 24. As used herein, "releasably affixed" refers to the condition of two or more components which may be attached and separated without destruction of or undue distortion to either component. The releasable wrapper 34 is preferably slightly larger than the central portion of the sanitary napkin 20 as it is defined by the longitudinal and lateral side margins 30 and 32.

Associated with the sanitary napkin 20 and each flap 28 is a means 40 for attaching the sanitary napkin 20 to the undergarment of a wearer. Particularly, each flap 28 may have its own adhesive patch 40b associated with the face of the flap 28 which contacts the undergarment of the wearer and, the central portion of the sanitary napkin 20 laterally intermediate the flaps 28 has adhesive 40a associated with the portion of the sanitary napkin 20 which contacts the undergarment of the wearer. More preferably such adhesive 40a and 40b are joined to the outwardly oriented face of the backsheet 24.

The releasable wrapper 34 contacts the adhesive 40a of the central portion of the backsheet 24, and if desired, the adhesive 40b of the flaps 28, to prevent contamination of such adhesive 40 prior to first use by the wearer. Also, the releasable wrapper 34 provides protection for the sanitary napkin 20 when it is inwardly trifolded and the releasable wrapper 34 is exposed.

Examining the components of the sanitary napkin 20 in more detail with continuing reference to FIG. 1, the sanitary napkin 20 has a generally centered longitudinal centerline 36. As used herein the term "longitudinal" refers to an imaginary line, axis or direction of the sanitary napkin 20, which line, axis or direction is typically centered between the side margins of the napkin and is generally aligned with the vertical plane which bisects a standing wearer into left and right body halves. The term "lateral" refers to an imaginary line, axis or direction generally orthogonal the longitudinal direction and within the plane of the sanitary napkin 20, and is generally sideways aligned relative to the wearer.

The topsheet 22 is the component of the garment which is oriented towards and contacts the body of the wearer and receives bodily discharges. The topsheet 22 is liquid pervious and should be flexible and nonirritating to the skin. As used herein the term "flexible" refers to materials which are compliant and readily conform to the shape of the body or respond by easily deforming in the presence of external forces. Preferably the topsheet 22 is not noisy, to provide discretion for the wearer. The topsheet 22 should be sanitary, clean in appearance and somewhat opaque to hide the bodily discharges collected in and absorbed by the core 26.

The topsheet 22 should further exhibit good strikethrough and rewet characteristics, permitting bodily discharges to rapidly penetrate the topsheet 22 to the core 26, but not flow back through the topsheet 22 to the skin of the wearer. Suitable topsheets 22 may be made from nonwoven materials and perforated polyolefinic films.

The topsheet 22 has a plurality of apertures to permit liquids deposited thereon to pass through to the core 26. Such apertures may, but need not, be present in the flaps 28. An apertured polyolefinic film topsheet 22 having about 5 to about 60 percent open area, typically about 25 percent open area, and a thickness of about 0.01 to about 0.05 millimeters prior to aperturing and about 0.46 to about 0.51 millimeters after aperturing is suitable.

If desired, the topsheet 22 may be sprayed with a surfactant to enhance fluid penetration to the core 26. The surfactant is typically nonionic and should be nonirritating to the skin. A surfactant density of about 0.01 milligrams per square centimeter of topsheet 22 area is suitable. A suitable surfactant is sold by the Glyco Chemical, Inc. of Greenwich, Conn. as "PEGOSPERSE" 200 ML.

A particularly suitable topsheet 22 may be made in accordance with U.S. Pat. No. 4,342,314 issued Aug. 3, 1982 to Radel et al. and U.S. Pat. No. 4,463,045 issued Jul. 31, 1984 to Ahr et al., which patents are incorporated herein by reference for the purpose of disclosing particularly preferred executions of liquid pervious topsheets. A topsheet 22 made of model X-3265 or model P1552 apertured formed film sold by the Ethyl Corporation, Visqueen Division, of Terre Haute, Ind. has been found to work well.

The backsheet 24 may be any flexible, liquid impervious or liquid resistant material, such as a polyolefinic film, and prevents discharges collected by and contained in the sanitary napkin 20, particularly discharges absorbed by the core 26, from escaping the sanitary napkin 20 and soiling the clothing and bedding of the wearer. Preferably the backsheet 24 is not noisy, to provide discretion for the wearer.

The backsheet 24 may also be impervious to malodorous gases generated by absorbed bodily discharges, so that the malodors do not escape and become noticed by the wearer. A low density polyethylene backsheet 24 about 0.01 to about 0.05 millimeters in thickness, preferably about 0.02 millimeters in thickness, has been found to work well. A polyethylene film, such as is sold by the Ethyl Corporation, Visqueen Division, under model XP-3985 has been found particularly well suited for this invention.

Further, the backsheet 24 may be made of a soft clothlike material which is hydrophobic relative to the topsheet 22, e.g., a polyester or polyolefinic fiber backsheet 24 works well. A particularly preferred soft, clothlike backsheet 24 material is a laminate of a polyester nonwoven material lamina and an uniaxially elastically extensible elastomeric film such as described in the aforementioned U.S. Pat. No. 4,476,180 issued to Wnuk.

In a particularly preferred embodiment, the backsheet 24 is slightly larger than the topsheet 22 and intermediate absorbent core 26. In such an embodiment, the topsheet 22 and intermediate absorbent core 26 are peripherally circumscribed by the backsheet 24 which has a radial margin of about 0.5 centimeters to about 1.5 centimeters, preferably about 1.0 centimeter, from the side margin of the topsheet 22. This geometry provides a marginal area of protection should the core 26 become overloaded or the sanitary napkin 20 otherwise fail. In such an embodiment the backsheet 24 and flaps 28 are preferably unitary and coextensive.

The backsheet 24 and the topsheet 22 are preferentially peripherally joined using known techniques, either entirely, so that the entire perimeter of the sanitary napkin 20 is circumscribed by such joining, or are partially peripherally joined. Any arrangement that provides for a unitary assembly and capture of the core 26 intermediate the topsheet 22 and backsheet 24 is suitable. Such an assembly has two mutually opposed major faces, one defined by the topsheet 22 and one defined by the backsheet 24.

The outwardly oriented face of the backsheet 24 preferably further comprises means 40 for attaching the sanitary napkin 20 to the undergarment of the wearer. Pressure sensitive adhesive 40*a* has been found to work well. Preferably a strip 40*a* of longitudinally oriented adhesive provides good protection against either the front or the back of the sanitary napkin 20 being detached from the wearer's undergarment. The strip 40*a* may be continuous or intermittent. A particularly preferred arrangement utilizes two longitudinally oriented strips 40*a*, one on each side of the longitudinal centerline 36. The strips 40*a*, or at least a portion thereof, can extend longitudinally outboard of the flaps 28, as shown in FIG. 1

The absorbent core 26 is the means for collecting and containing bodily discharges, particularly menses, deposited thereon or which otherwise traverse through the liquid permeable topsheet 22. The core 26 is the component of the sanitary napkin 20 which receives and retains the bodily discharges. The core 26 is conformable and nonirritating to the skin, and preferably relatively thin. The core 26 may be rectangularly or hourglass shaped. The core 26 preferably has two opposed faces, one oriented towards the backsheet 24 and one oriented towards the topsheet 22.

Suitable core 26 materials include combinations of airfelt, such as cellulose wadding, and fibrated communition pulp; layers of tissue paper; and absorbent gelling materials. If a tissue paper core 26 is selected, tissue paper made in accordance with U.S. Pat. No. 4,191,609 issued Mar. 4, 1980 to Trokhan and incorporated herein by reference to show a particularly preferred tissue paper suitable for the core 26 of the sanitary napkin 20 described herein.

The core 26 need not have a total absorbent capacity much greater than the total amount of bodily discharges to be absorbed. The core 26 is preferably narrow and thin, to be comfortable to the wearer. For the embodiment described herein the capacity of the core 26 should be at least about 2 grams of 0.9 percent saline solution. Suitable saline solution is sold by Travenol Laboratories of Deerfield, Ill.

If it is desired to incorporate absorbent gelling materials into the core 26 of the sanitary napkin 20, absorbent gelling materials made in accordance with U.S. Pat. Redesign No. 32,649 issued Apr. 19, 1988 to Brandt et al. and incorporated herein by reference for showing particularly preferred absorbent gelling materials are suitable. A suitable core 26 comprises a laminate of absorbent gelling materials and tissue may be purchased from the Grain Processing Corporation of Muscatine, Iowa under Model Number L535.

The core 26 should be sized to register with the topsheet 22 and backsheet 24. The core 26 is preferably interposed between the topsheet 22 and backsheet 24 to prevent the absorbent material of the core 26 from shredding or becoming detached while the sanitary napkin 20 is worn and to ensure proper containment of bodily discharges. This arrangement also provides for a unitary assembly.

The core 26 is preferentially joined to the topsheet 22, and may be joined to the backsheet 24. The term "joined" refers to the condition where a first member or component is affixed, or connected, to a second member or component either directly; or indirectly, where the first member or component is affixed, or connected, to an intermediate member or component which in turn is affixed, or connected, to the second member or component. The joined relationship between the first member, or component, and the second member, or component, is intended to remain for the life of the sanitary napkin 20.

Joining is preferentially accomplished by adhesive bonding the core 26 to the topsheet 22 or the backsheet 24. The adhesive (not shown) may be applied in any suitable spray pattern, such as a spiral, or in longitudinally oriented beads. The adhesive should be surfactant resistant and of low pressure sensitivity, so as not to stick to the skin of the wearer.

The sanitary napkin 20 preferably has a caliper of less than about 4 millimeters and more preferably less than about 2 millimeters, as measured with a comparator gage having an approximately 80.0 gram test weight and an approximately 10.0 gram comparator foot having a diameter of about 2.54 centimeters and a contact surface area of approximately 5.1 square centimeters. Also, the sanitary napkin 20 of the present invention should have a topsheet 22 surface area of at least about 100 square centimeters to prevent discharged fluids from missing the target area. The sanitary napkin 20 may also comprise a flap 28 extending from a longitudinal side margin 30 of the sanitary napkin 20, and preferably one flap 28 extending from each longitudinal side margin 30 of the sanitary napkin 20. The flaps 28 have a proximal end 44 which is typically coincident with the juncture of attachment of the flap 28 to the longitudinal side margin 30 of the sanitary napkin 20. Alternatively, the proximal end 44 of the flap 28 may be joined to the sanitary napkin 20 at another location, remote from but juxtaposed with the longitudinal side margin 30. For example, as shown in FIG. 1, the proximal end 44 is located between one longitudinal side margin 30 and the longitudinal centerline 36 of the sanitary napkin 20.

The flaps 28 extend laterally outwardly from the sanitary napkin 20 and terminate at a distal end 46 which represents the portion of the flaps 28 furthest from the longitudinal side margins 30 of the sanitary napkin 20. The distal ends 46 of the flaps 28 are directed away from the longitudinal centerline 36 and central portion of the sanitary napkin 20. As used herein the phrase "central portion" refers to that part of the sanitary napkin 20 intermediate, particularly laterally intermediate, and defined by the proximal ends 44 of the flaps 28. The flaps 28 may be of any shape desired, with a particularly preferred shape being shown in FIG. 1.

The flaps 28 may be comprised of an integral and contiguous extension of the topsheet 22, the backsheet 24, or a laminate of both 22 and 24. Alternatively, the flaps 28 may be made of a separate and independent piece of material joined to the longitudinal side margins 30 of the sanitary napkin 20. Each flap 28 has one face generally coextensive of the topsheet 22 and a mutually opposed face generally coextensive of the backsheet 24. A face of the flap 28 is considered to be coextensive of the topsheet 22 or the backsheet 24 if a line having a lateral component can be drawn from the topsheet 22 or the backsheet 24, respectively, which does not cross a portion of the side margins 30 or 32 at the perimeter of the central portion of the sanitary napkin 20, unless such portion of the side margins 30 or 32 is generally longitudinally adjacent the proximal end 44 of the flap 28.

The flaps 28 preferably have a means 40 for attaching one face of the flap 28 to the wearer's undergarment or to the other flap 28. The attachment means 40 may be a mechanical fastener or, preferably, pressure sensitive adhesive 40*b*. If pressure sensitive adhesive 40b is selected, it should be disposed on the face of the flap 28 generally coextensive of the backsheet 24 so that when the flaps 28 are wrapped around the crotch portion of the wearer's undergarment, the adhesive 40b will face the outside of the wearer's undergarment. A generally rectangular patch of adhesive 40b on each flap 28, about 25 millimeters × 20 millimeters in size, works well. Suitable pressure sensitive adhesive 40 is sold by the Anchor Continental, Inc., 3 Sigma Division of Covington, Ohio as 0.02 millimeter pass with Century Adhesive A305-4.

For packaging, the flaps 28 are folded over the topsheet 22 so that the flaps 28 are in the topsheet facing relationship of FIG. 2. The flaps 28 are considered to be in a topsheet facing relationship if a line generally perpendicular the plane of the sanitary napkin 20 drawn outwardly from the topsheet 22 intercepts either face of the flap 28. The flaps 28 are preferably folded about the proximal edge 44 so that maximum coverage of the topsheet 22 is obtained. This arrangement provides a larger area of the topsheet 22 covered by the flaps 28, particularly the area of the topsheet 22 which is generally registered with the wearer's vagina, so that a sanitary and clean appearance of this portion of the topsheet 22 is promoted. It is not necessary that the flaps 28 be folded about the proximal ends 44, that the flaps 28 be in contacting relationship with the topsheet 22, or that no other folds occur between the distal and proximal ends 44 and 46 of the flaps 28. It is only necessary that the flaps 28 face towards the topsheet 22 and discourage outside contamination from readily soiling the portion of the topsheet 22 covered by the flaps 28.

Folding the flaps 28 in the configuration of FIG. 2 exposes the patch 40b of adhesive on the face of the flaps 28 generally coextensive of the backsheet 24. To prevent contamination and blocking of this adhesive patch 40b, each flap 28 may be covered with a separate and dedicated piece of release liner 41.

It will be apparent to one skilled in the art, however, that the flaps 28 may be folded over the backsheet 24 or, convolutely folded so that one flap 28 overlays the topsheet 22 and the other flap 28 overlays the backsheet 24. All such embodiments are within the spirit and scope of the claimed invention.

The releasable wrapper 34 has a perimeter defined by longitudinal edges and lateral edges. Preferably, the lateral edges of the releasable wrapper 34 are juxtaposed with the respective lateral side margins 32 of the sanitary napkin 20. This arrangement provides a releasable wrapper 34 having sufficient longitudinal extent to conceal and to protect the sanitary napkin 20 in the later described folded configurations.

The wrapper 34 has opposed faces. One face is an inwardly oriented face which is oriented towards the adhesive 40 and the outwardly oriented face of the backsheet 24. The other face is an outwardly oriented face opposed to the inwardly oriented face and which is oriented away from the sanitary napkin 20.

Preferably, the inwardly oriented face is release coated, to facilitate easy and convenient manipulation of the releasable wrapper 34, and particularly separation from the adhesive 40. Silicone releases, as are well known in the art, have been found to work well. The releasable wrapper 34 may be zone coated with the release coating only in the areas of the adhesive 40a and 40b, or may be entirely release coated throughout the inwardly oriented face as desired.

The releasable wrapper 34 may be made of kraft paper, calendered paper, or other materials as are well known in the art without departure from the spirit and scope of the claimed invention. A particularly preferred releasable wrapper 34 is made of machine glazed or machine finished paper having a basis weight of about $40.7 \times 10^{-3}$ kilograms per square meter (25 pounds per 3,000 square feet). The inwardly oriented face of the wrapper may be coated with a release coating such as silicone. Suitable release coatings are marketed by Akrosil of Menasha, Wis. as "SILOX" 4R/O and "SILOX" C1S.

With continuing reference to FIG. 2, it can be seen that the releasable wrapper 34 wraps at least one, and preferably each, longitudinal side margin 30 of the sanitary napkin 20 in a C-fold 50. As used herein, a "C-fold" refers to the configuration of a component which is folded over itself to provide a double thickness and may have a foreign component interposed between the layers of the folded component. As illustrated in FIG. 2, it is preferred that the sanitary napkin 20 and releasable wrapper 34 be equivalently and symmetrically disposed and folded about the longitudinal centerline 36.

In the C-folded arrangement of FIG. 2, the entire backsheet 24 is covered by the releasable wrapper 34 and a portion of the topsheet 22 juxtaposed with the longitudinal side margins 30 are also covered by the releasable wrapper 34. As used herein, "releasable" refers to the condition where a first component may be separated from a second component at least once without causing destruction or undue distortion of either component.

The illustrated arrangement provides the advantage that one entire major face, particularly the face associated with the backsheet 24, is protected by the releasable wrapper 34, the longitudinal side margins 30 of the sanitary napkin 20 are likewise protected, and additionally a portion of the topsheet 22 is protected by the releasable wrapper 34. Further, in this arrangement no significant portion of the releasable wrapper 34 extends laterally outboard of the sanitary napkin 20, obviating the need for a bulky package, or a region of the releasable wrapper 34 to be dedicated for sealing of the package.

As illustrated in FIG. 3, the sanitary napkin 20 and releasable wrapper 34 may be folded about two spaced-apart laterally oriented fold lines. As used herein, the phrase "spaced-apart laterally oriented fold lines" refers to longitudinally offset lines, generally parallel the lateral direction, and about which the sanitary napkin 20 and releasable wrapper 34 are commonly folded.

Folding the sanitary napkin 20 about the spaced-apart laterally oriented fold lines produces a folded arrangement defining three trisections 51 and 52, a central trisection 51 intermediate and bounded by two outboard trisections 52. The outboard trisections 52 may be more specifically described as an inner-outboard trisection 52a and an outer-outboard trisection 52b. As used herein, inner and outer outboard trisections 52 are described relative to the central trisection 51 when the sanitary napkin 20 and releasable wrapper 34 are in the folded arrangement of FIG. 4. The inner-outboard trisection 52a is generally adjacent the central trisection 51 and intermediate such central trisection 51 and the outer-outboard trisection 52b. Conversely, the outer-outboard trisection 52b is relatively further from the central trisection 51 due to the interposition of inner-outboard trisection 52a.

In the folded arrangement of FIG. 4, the package defines two mutually opposed major surfaces, one defined by the outer-outboard trisection 52b, and one defined by the central trisection 51. The arrangement of FIG. 4 produces a sanitary napkin 20 having an e-fold with a releasable wrapper 34 having a corresponding e-fold. The releasable wrapper 34 is preferably of sufficient longitudinal dimension to overlie one outboard trisection 52 and the central trisection 51. More preferably, the releasable wrapper 34 is of sufficient longitudinal dimension to overlie all three trisections 51 and 52, so that no adhesive 40a is exposed.

Referring back to FIG. 1, the releasable wrapper 34 may further comprise a means for maintaining the sanitary napkin 20 and releasable wrapper 34 in the aforementioned folded arrangement. Suitable means for maintaining the folded arrangement include hook and loop mechanical fasteners, such as are sold under the trademark "VELCRO"; adhesive tabs, such as are illustrated in the prior art, or, preferably adhesive 54 juxtaposed with the longitudinal edge of the releasable wrapper 34.

Preferably the adhesive 54 is placed on the longitudinal edge of the releasable wrapper which overlays and faces outwardly from the topsheet 22. In one execution, the adhesive 54 may be applied to the outboard trisections 52 so that when the inner-outboard trisection 52a is folded over the central trisection 51 such trisections 51 and 52a are releasably affixed to each other and adhesive is juxtaposed with the outer-outboard trisection 52b so that it may be releasably affixed to the inner-outboard trisection 52a. Alternatively, the adhesive 54 may be applied to the central and outer-outboard trisections 51 and 52b.

In one variation, the adhesive 54 may further comprise and be disposed on a tab 55 longitudinally extending beyond the lateral edge of the outer-outboard trisection 52a. The adhesive 54 of the tab 55 not longitudinally beyond such lateral edge is affixed to the exposed face of the outer-outboard trisection 52b.

The adhesive 54 may be applied in a continuous strip (as shown), in an intermittent strip, or may be a single spot. It is not critical which form the adhesive 54 is applied, only that it have sufficient peel strength to maintain the folded arrangement until it is desired to conveniently open the sanitary napkin 20 and releasable wrapper 34 for the first use by the wearer.

Figure 5:
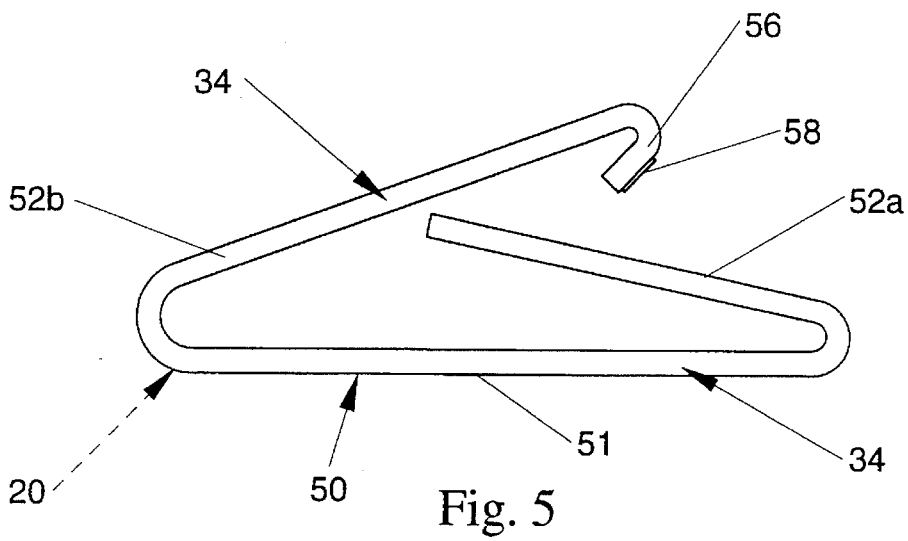
FIG. 5 is a profile vertical elevational view of a variant embodiment having the releasable wrapper folded over one lateral side margin of the sanitary napkin.

FIG. 5 illustrates a variant embodiment of the invention wherein the releasable wrapper 34 has a longitudinal extension 56 which overlays at least one, and if desired both, lateral side margins 32 of the sanitary napkin 20. This arrangement provides further protection for the sanitary napkin 20.

If only one longitudinal extension 56 is utilized, preferably, but not necessarily, it overlays the lateral side margin 32 of the outer-outboard trisection 52b. A means to maintain the sanitary napkin 20 and releasable wrapper 34 in the desired folded arrangement may also be advantageously employed with the longitudinal extension 56. In one particularly preferred arrangement, adhesive 58 is disposed on the longitudinal extension 56, particularly on the folded face of the longitudinal extension 56 which faces outwardly and away from the topsheet 22 when the sanitary napkin 20 is not in a folded arrangement and faces towards the opposed outboard trisection 52 when the sanitary napkin 20 and releasable wrapper 34 are folded.

The adhesive 58 may be juxtaposed with the longitudinal edges of the longitudinal extension 56, or generally coincide with the longitudinal centerline, or be positioned on the longitudinal extensions 56 generally coextensive of the longitudinal centerline 36. Using either arrangement, the longitudinal extension 56 of the releasable wrapper 34 is adhered to a portion of the releasable wrapper 34 which is longitudinally inboard of the lateral side margins 32 of the sanitary napkin 20.

Figure 6:
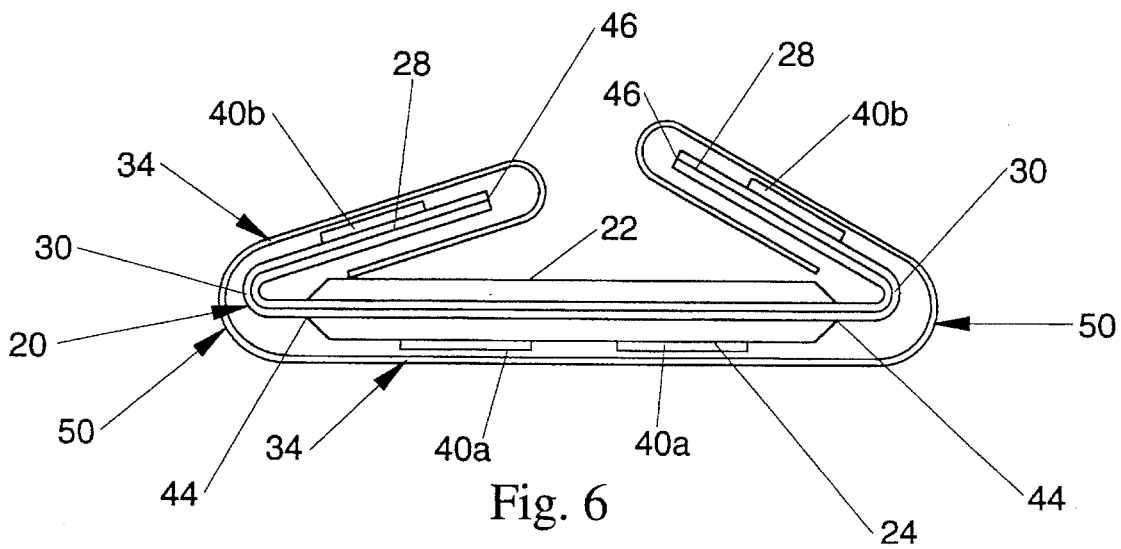
FIG. 6 is an endwise vertical elevational view of a releasable wrapper which encases both faces of the flaps of the sanitary napkin of FIG. 1.

FIG. 6 illustrates a variation which provides yet additional protection for a sanitary napkin 20 having flaps 28. In FIG. 6, the releasable wrapper 34, in addition to C-folding the longitudinal side margins 30 of the sanitary napkin 20, extends laterally inboard to the distal ends 46 of the flaps 28, and C-folds the distal end 46 of one, and preferably of both, flaps 28 of the sanitary napkin 20. The releasable wrapper 34 of such a configuration has a segment interposed between the flap 28 and the topsheet 22. Providing the releasable wrapper 34 extends longitudinally outboard of and between both lateral side margins 32, and the two C-folds 50 which overlay the distal ends 46 of the flaps 28 meet or overlap, the entire sanitary napkin 20 is protected by the releasable wrapper 34 without the necessity of trifolding about spaced apart laterally oriented fold lines.

Figure 7:
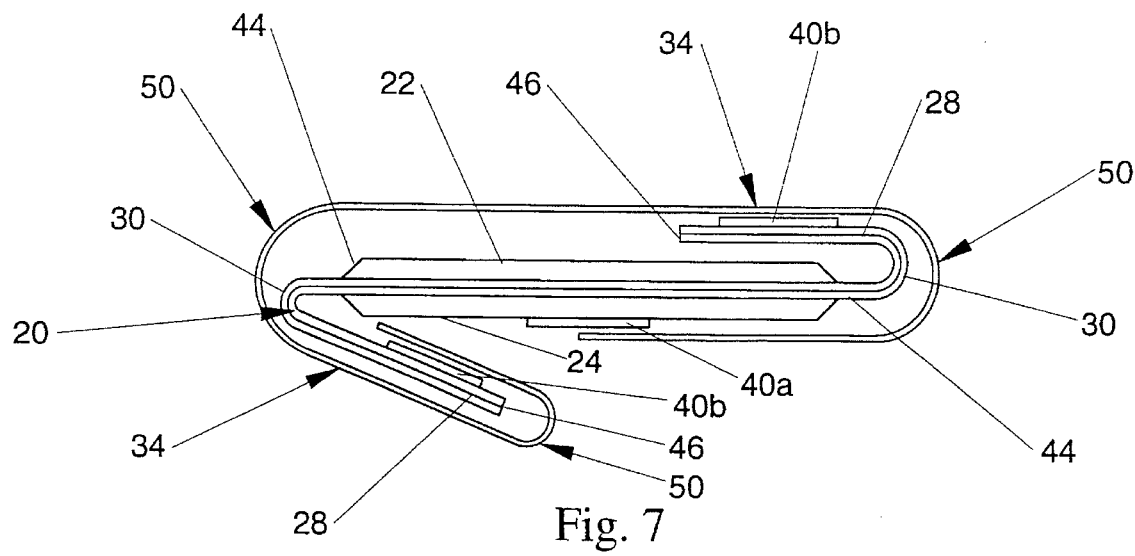
FIG. 7 is an endwise vertical elevational view of a sanitary napkin having one flap folded over the topsheet, one flap folded over the backsheet, and a releasable wrapper which C-folds both faces of one flap and both longitudinal side margins.
Figure 8:
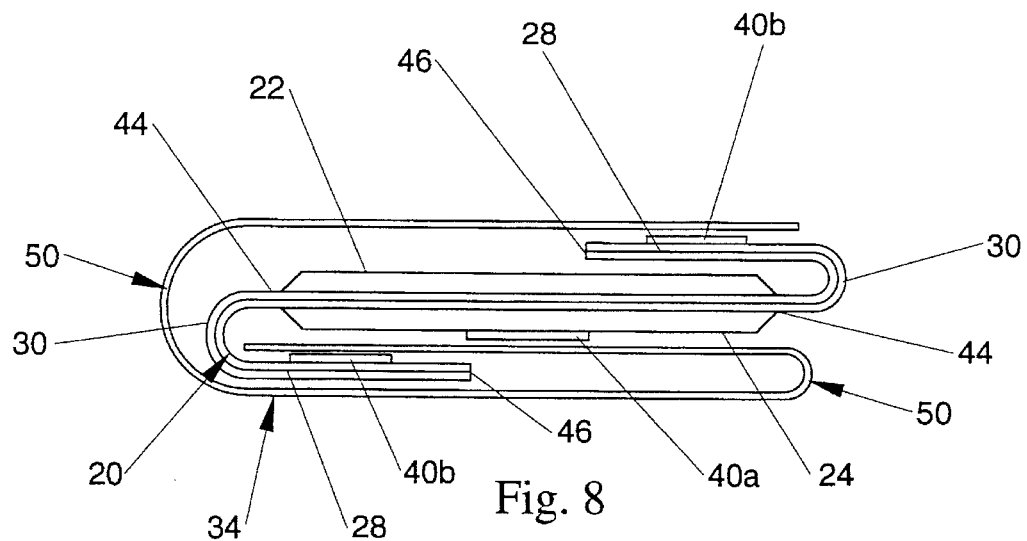
FIG. 8 is an endwise vertical elevational view of a sanitary napkin having one flap folded over the topsheet, one flap folded over the backsheet, and a releasable wrapper which encases both faces of one flap and resembles an e-fold.
Figure 9:
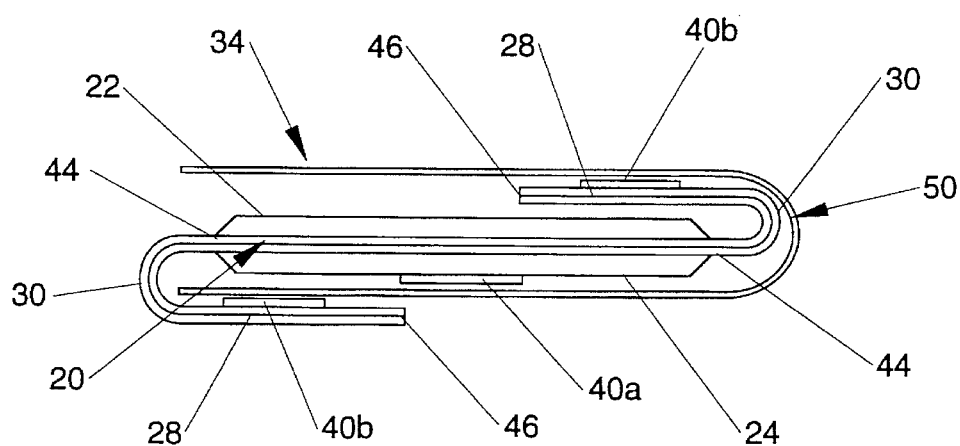
FIG. 9 is an endwise vertical elevational view of a sanitary napkin having one flap folded over the topsheet, one flap folded over the backsheet, with one flap being inside the releasable wrapper and one flap being outside the releasable wrapper.

FIGS. 7–9 generally illustrate embodiments where both flaps 28 of the sanitary napkin 20 are not folded over the same major face defined by the topsheet 22 and the backsheet 24. In the variations illustrated by FIGS. 7–9, the sanitary napkins 20 have one flap 28 folded over the topsheet 22, and the other flap 28 folded over the backsheet 24 in a convolute fold pattern.

At least one, and preferably both, flaps 28 of the sanitary napkins 20 of FIG. 7–9 have adhesive 40b associated with, and preferably joined to, the face of the flaps 28 which is generally coextensive of the backsheet 24. The flap 28 folded over the topsheet 22 will have the adhesive 40b of the flap 28 facing outwardly, where this adhesive 40b may be covered and protected by the releasable wrapper 34. If the flap 28 folded over the backsheet 24 also has adhesive 40b, such adhesive 40b is preferably covered by an independent piece of release paper (not shown). However, the flap 28 having adhesive 40b exposed by the selected convolute fold arrangement, may advantageously use the releasable wrapper 34 to cover such adhesive 40b, and, as well, cover the adhesive 40a associated with the central portion of the backsheet 24.

In the embodiment of FIG. 7, the one flap 28 of the sanitary napkin 20 has its distal end 46 wrapped in a C-fold 50 by the releasable wrapper 34. The corresponding first longitudinal side margin 30 of the sanitary napkin 20 is wrapped in a second C-fold 50. The remainder of the releasable wrapper 34 laterally extends across the sanitary napkin 20, covers the other flap 28, wraps the opposite longitudinal side margin 30 in a third C-fold 50 and extends laterally inwardly towards the longitudinal centerline, to approach the distal end 46 of the flap 28 of the first longitudinal side margin 30. If desired, the longitudinal edge of the releasable wrapper 34 which approaches the distal end 46 of such first flap 28 may overlap the portion of the releasable wrapper 34 which C-folds the distal end 46 of the flap 28.

It is to be understood by one skilled in the art that the first C-fold 50 of the releasable wrapper 34, which wraps the distal end 46 of the one flap 28, need not have its apex close to the distal end 46 (as illustrated), but rather this apex may be laterally displaced therefrom towards the opposite longitudinal side margin 30. As the apex of the C-fold 50 which wraps the distal end 46 of the one flap 28 approaches the opposite longitudinal side margin 30, a greater portion of the major face which such flap 28 overlays is covered and protected by a double thickness of the releasable wrapper 34. If desired, the releasable wrapper 34 of such a variant may be generally coterminous with, or laterally outboard of, such opposite longitudinal side margin 30 rather than be disposed laterally inboard of such opposite longitudinal side margin 30 as illustrated.

In the variation of FIG. 8, the releasable wrapper 34 has a first C-fold 50 wrapping the distal end 46 of either flap 28, and wraps the corresponding longitudinal side margin 30 of the sanitary napkin 20 in a second C-fold 50. The releasable wrapper 34 extends generally uninterrupted across a major face of the sanitary napkin 20, particularly the major face opposite that which the C-folded flap 28 is folded.

The lateral edge of the releasable wrapper 34 may be generally coextensive with the other longitudinal side margin 30 (as illustrated). It will be recognized that the backsheet 24 may have adhesive 40a covered by an independent release paper (not shown) or may have such adhesive 40a adhered to the inwardly oriented face of the releasable wrapper 34 (as illustrated). Furthermore, the apex of the first C-fold 50 which wraps the distal end 46 of the flap 28 may be adjacent such distal end 46 rather than adjacent the opposite longitudinal side margin 30, or may be at any intermediate position. If a major face of the sanitary napkin is exposed, as not illustrated by FIG. 8, preferably the exposed face is that face defined by the backsheet 24, so that the topsheet 22 is protected and remains in a sanitary condition.

FIG. 9 illustrates a releasable wrapper 34 which wraps one longitudinal side margin 30 of the sanitary napkin 20 in a C-fold 50 and covers the flap 28 corresponding to this longitudinal side margin 30. It is to be understood by one skilled in the art that the other longitudinal side margin 30 could be wrapped in a C-fold 50 as well, by an extension of the portion of the releasable wrapper 34 which covers such flap 28. A longitudinal edge of the releasable wrapper 34 is interposed between the other flap 28 and the major surface which the other flap 28 overlays.

In yet a further variation, the sanitary napkin 20 is folded in an S-fold about two spaced-apart transversely oriented fold lines, so that the topsheet 22 of one outboard trisection 52 faces outwardly and is exposed, and the backsheet 24 of the other outboard trisection 52 faces outwardly and is exposed. In an S-folded configuration, the releasable wrapper 34 may be somewhat shorter than the unfolded longitudinal dimension of the sanitary napkin 20, providing the releasable wrapper 34 is applied to the sanitary napkin 20 after it is S-folded.

With an S-folded sanitary napkin 20, the releasable wrapper 34 may overlay the trisection 52 which has the exposed topsheet 22, so that the topsheet 22 is completely covered, and wrap the longitudinal side margins 30 of the sanitary napkin 20 in C-folds 50. The longitudinal edges of the releasable wrapper 34 then overlay the backsheet 24 of the other exposed trisection 52. A feature common to this and any of the foregoing embodiments is that the longitudinal edges of the releasable wrapper 34 may be spaced apart, abut, or overlap as desired.

If desired, the S-folded sanitary napkin 20 may be rotated 90 degrees relative to the releasable wrapper 34, so that the longitudinal axes of the sanitary napkin 20 and the releasable wrapper 34 are mutually orthogonal. The S-folded sanitary napkin 20 is placed on the releasable wrapper 34 so that the trisection 52 of the sanitary napkin 20 having the exposed topsheet 22 is completely covered. One apex of the S-fold and a lateral side margin 32 is then wrapped by the releasable wrapper 34 in a C-fold 50. In this arrangement, the longitudinal edges of the releasable wrapper 34 bound the exposed backsheet 24 as described above. It will be apparent that this arrangement may be transposed, so that the releasable wrapper 34 overlays the backsheet 24 and the longitudinal edges of the releasable wrapper 34 overlay the topsheet 22.

With each of the S-folded sanitary napkin embodiments, the releasable wrapper 34 does not conform to a similar S-fold, but rather is generally U-shaped. This produces a somewhat shorter releasable wrapper 34 because the central trisection 51 of the sanitary napkin 20 does not have a dedicated length of releasable wrapper 34.

It will be apparent to one skilled in the art that other variations are feasible and within the spirit and scope of the claimed invention. For example, combinations of the foregoing embodiments are feasible, and other means for maintaining the sanitary napkin 20 within the folded arrangement may be utilized. Additionally, other asymmetric arrangements may be utilized and adjustments in the relative sizes of the sanitary napkin 20 and releasable wrapper 34 may be made to accommodate the desired package size. All such variations are within the scope of the claimed invention.

What is claimed is:

1. An individually wrapped sanitary napkin for wearing in a crotch region of an undergarment, said individually wrapped sanitary napkin comprising:

a sanitary napkin having two major mutually opposed faces and a longitudinal centerline said sanitary napkin comprising:

a central portion having two opposed longitudinal side margins and two opposed lateral side margins defining the perimeter of said central portion, said central portion comprising:

a liquid pervious topsheet defining one major face of said sanitary napkin;

a liquid impervious backsheet defining the other major face of said sanitary napkin, said backsheet having opposed inwardly and outwardly oriented faces, and being joined to said topsheet;

an adhesive patch on said outwardly oriented face of said backsheet;

an absorbent core positioned between said topsheet and said backsheet; and two flaps for folding under the undergarment, each said flap having a proximal edge between one said longitudinal side margin of said central portion and said longitudinal centerline of said sanitary napkin and being joined to said central portion at said proximal edge, each said flap extending laterally from said proximal edge to a distal edge lying outboard of said one longitudinal side margin of said central portion, said flaps being folded over one of said topsheet or said backsheet so that said distal edges of said flaps are intermediate said longitudinal side margins of said central portion; and a releasable wrapper disposed on said sanitary napkin, said releasable wrapper having two longitudinal side margins and two ends, one end of said releasable wrapper being juxtaposed with a lateral side margin of said central portion of said sanitary napkin, said releasable wrapper being generally laterally centered on the longitudinal centerline of the other of said topsheet or said backsheet, and wrapping said longitudinal side margins of said central portion of said sanitary napkin in a first C-fold oriented towards said longitudinal centerline, and wrapping the distal edges of said flaps in a second C-fold oriented towards said longitudinal side margins of said central portion of said sanitary napkin so that said longitudinal side margins of said wrapper are interposed between said flaps and the one of said topsheet or said backsheet that said flaps are folded over.

* * * * *